US006835186B1

(12) United States Patent
Pennington et al.

(10) Patent No.: US 6,835,186 B1
(45) Date of Patent: Dec. 28, 2004

(54) MECHANICAL BREAKUP UNIT FOR BIOCHEMICALLY REACTIVE FLUID DELIVERY DEVICE

(75) Inventors: David W. Pennington, Fox Lake, IL (US); Atif M. Yardimci, Northbrook, IL (US); David Amrani, Glendale, WI (US); Arnold C. Bilstad, Deerfield, IL (US); Yves A. Delmotte, Neufmaison (BE); James P. Diorio, Antioch, IL (US); Robert L. Petersen, Winthrop Harbor, IL (US); Joseph F. Prybell, Grayslake, IL (US); James Slepicka, Spring Grove, IL (US); Cristina Stadler, Columbus, IN (US); John Womelsdorf, Caldwell, NJ (US)

(73) Assignee: Baxter International, Inc., Deerfield, IL (US)

( * ) Notice: Subject to any disclaimer, the term of this patent is extended or adjusted under 35 U.S.C. 154(b) by 276 days.

(21) Appl. No.: 09/669,353

(22) Filed: Sep. 26, 2000

Related U.S. Application Data

(63) Continuation-in-part of application No. 09/386,198, filed on Aug. 31, 1999, now Pat. No. 6,461,325, which is a continuation-in-part of application No. 08/679,658, filed on Jul. 12, 1996, now Pat. No. 5,989,215, which is a continuation-in-part of application No. PCT/EP96/00160, filed on Jan. 16, 1995.

(30) Foreign Application Priority Data

Jan. 16, 1995 (DE) .......................................... 195 01 067

(51) Int. Cl.⁷ ............................................. A61M 37/00
(52) U.S. Cl. ......................................................... 604/82
(58) Field of Search ................................ 604/82–86, 88, 604/89, 90, 91, 92, 93.01, 94.01, 118, 131, 181, 187, 264, 266, 268, 43, 191, 275

(56) References Cited

U.S. PATENT DOCUMENTS

| 5,582,596 | A | * | 12/1996 | Fukunaga et al. | .......... 604/191 |
| 5,989,215 | A | * | 11/1999 | Delmotte et al. | ............. 604/82 |
| 6,063,055 | A | * | 5/2000 | Epstein et al. | ................ 604/82 |
| 6,121,341 | A | * | 9/2000 | Sawhney et al. | ............. 522/84 |
| 6,328,229 | B1 | * | 12/2001 | Duronio et al. | ............. 239/399 |

* cited by examiner

Primary Examiner—Christopher L. Chin
Assistant Examiner—Ann Y. Lam
(74) Attorney, Agent, or Firm—Bruce M. Canter; Stradling Yocca Carlson & Rauth (57) ABSTRACT

This invention provides a medical device for delivering volumetric quantities of a first and a second biochemically reactive fluid in which separate MBUs atomize the fluids. The device of the present invention includes a fluid delivery device for laparoscopically delivering fluids having two feed conduits for delivering fluid to feed ports of the mechanical breakup units, the mechanical breakup units having two feed ports for receiving fluid from the feed conduits and directing such fluid into spin chambers and funneling portions having a sloped sidewall for directing fluid from the spin chambers through an exit port. The device is suitably dimensioned for creating a spray of two fluids with different viscosities such as fibrinogen and thrombin in such a manner that the thrombin spray cone encompasses the fibrinogen spray cone at a distance of about one inch from the exit port with a 0.5 cc/second flow rate to avoid depositing unreacted fibrinogen on a surface. Other instruments such as optical fibers may be incorporated within the device.

3 Claims, 10 Drawing Sheets

80 psi

MECHANICAL BREAKUP UNIT FOR BIOCHEMICALLY REACTIVE FLUID DELIVERY DEVICE

RELATED APPLICATIONS

This application is a continuation-in-part of U.S. patent application Ser. No. 09/386,198, filed Aug. 31, 1999, now U.S. Pat. No. 6,461,325, which in turn is a continuation-in-part of U.S. patent application Ser. No. 08/679,658, filed Jul. 12, 1996, now U.S. Pat. No. 5,989,215, issued Nov. 23, 1999, from International Patent Application No. PCT/EP96/00160, filed Jan. 16, 1995, which claims priority from the German patent application number 195 01 067.1, also filed on Jan. 16, 1995

TECHNICAL FIELD

This invention relates to a mechanical breakup unit (MBU) for atomizing biochemically reactive fluids, and more particularly, a MBU in a medical fluid delivery device for separately atomizing fibrinogen and thrombin contained in separate containers to form fibrin on a surface.

BACKGROUND ART

One of the major problems in intra-abdominal surgery is the avoidance of post-operative adhesions. It is well-known that adhesions contribute to pain, immobility, retarded wound healing, and in particular to intestinal obstruction which may even be life-threatening. In the field of gynecological surgery, post-surgical adhesions involving female reproductive organs may result in infertility.

Each surgical procedure necessarily produces various forms of trauma where the abdominal cavity or other human cavity is opened. Physiologically, the process of wound closure then starts when bleeding ceases upon formation of a hemostatic clot at the areas of blood vessel injury. The clot, at first comprising mainly platelets, is solidified by a natural fibrin network resulting from the activation of an enzyme cascade involving thrombin, factor XIII and calcium. Further steps on the way to the sealing of the wound are retraction of the hemostatic clot, invasion of various cell types including fibroblasts into the wound area and eventually the lysis of the fibrin network. Adhesions are thought to begin forming when the fibrin clot covering an injury comes into contact with an adjacent surface and the new connective tissue produced by the fibroblasts attaches the two surfaces together.

This sometimes painful condition may often require a further operative procedure for removing/lysing the adhesions, called adhesiolysis, which, like the first operation, introduces the risk of forming additional adhesions.

Accordingly, the prevention of adhesion formation is medically important. Among the different approaches for prevention of adhesion formation, one involves the use of materials as a physical or bio-mechanical barrier for the separation or isolation of traumatized tissues during the healing process. Both synthetic materials and natural materials have been used as a barrier to adhesion formation. Some permanent inert implants, like GoreTex® surgical membranes consisting of expanded polytetra-fluoroethylene (PTFE) generally require a second operative procedure to remove them, while others, such as surgical membranes of oxidized regenerated cellulose, are biodegradable but are thought to elicit an inflammatory response ultimately leading to adhesion formation (A. F. Haney and E. Doty, *Fertility and Sterility,* 60, 550–558, 1993).

Fibrin sealants/glues are well-known in the art for use in hemostasis, tissue sealing and wound healing, and have been commercially available outside the United States for more than a decade. Fibrin glues have not been used for anti-adhesion purposes. Further, the practice of changing the concentrations of thrombin and fibrinogen to achieve a fibrin film having a desired pore size has also not been practiced.

Fibrin glues mimic the last step of the coagulation cascade and are usually commercialized as kits comprising two main components. The first component is a solution comprising fibrinogen and factor XIII, while the second component is a thrombin calcium solution. After the mixing of components, the fibrinogen is proteolytically cleaved by thrombin and thus converted into fibrin monomers. Factor XIII is also cleaved by thrombin into its activated form (FXIIIa). FXIIIa cross links the fibrin monomers to form a three-dimensional network commonly called "Fibrin Gel."

Previous attempts to provide a thrombin and fibrinogen delivery device are known. For example, one such device is disclosed in U.S. Pat. No. 4,978,336 to Capozzi et al. which discloses a dual syringe system. A device made by the assignee of the '336 patent, Hemaedics, Inc., is sold under the tradename DUOFLO. The distal end of each syringe is attached to a common manifold having a mixing chamber. Fibrinogen and thrombin solutions are mixed in the manifold 14 prior to application to a wound or other surface. The manifold has a discharge tip for delivering the mixed solution onto a surface. A shortcoming of this device is the propensity for the tip to clog with solid fibrin being formed during brief interruptions in the application process—such interruptions are common in medical procedures. The likelihood of this occurring increases as the thrombin concentration increases especially thrombin concentrations of greater than 20 IU/ml. The '336 patent acknowledges the clogging problem and suggests solving the problem by replacing the clogged tip. (Col. 3, line 4–Col. 4, line 2). However, replacing clogged tips is impractical and unacceptable for minimally invasive surgeries where a cavity of an animal body is accessed through a small surgical opening.

Other techniques teach applying beads of a solution of thrombin and calcium adjacent in contact with a solution of fibrinogen and Factor XIII on a surface. In such a case, the thrombin and fibrinogen react primarily along interfacing surfaces while the remaining portions of the solutions are generally isolated from one another by the solid fibrin formed between them. Thus, there is inadequate mixing of the solutions to provide for a suitable fibrin film. Further, the unreacted fibrinogen is now available to react with thrombin supplied by the body to promote the formation of adhesions.

U.S. Pat. No. 4,631,055 discloses another thrombin and fibrinogen delivery device having two syringes mounted in a holding frame in a parallel spaced relationship. A conical portion of a distal end of each syringe is inserted into a connecting head. In one embodiment of the '055 patent, mixing of fluids contained in each syringe occurs inside the connecting head and in another embodiment the mixing of the fluids occurs outside the mixing head. The connecting head also includes a channel to supply medicinal gas under pressure. The medicinal gas contacts the fluids at a mouth of the connecting head and conveys the fluids contained in the syringes to a surface.

Product literature commenting on a dual syringe device for delivering fibrinogen and thrombin and sold by the assignee of the '055 patent, reports that the device operates at gas pressures of about 30–65 psi. If such devices are not properly used, the momentum of the pressurized gas, especially when conveying entrained fluids, could cause damage to tissue being treated by this device.

Two known devices in the prior art are disclosed in U.S. Pat. Nos. 5,368,563 to Lonneman et al. and 5,582,596 to Fukunaga et al. The '563 patent discloses a large sprayer assembly in FIGS. 1–9 having a lateral feed conduit connecting two syringe connections to two mechanical breakup units. The syringes may contain separately a solution of fibrinogen and a solution of thrombin which are mixed to produce fibrin. The '563 patent does not concern itself, however, with the possibility of unreacted fibrinogen. Further, due to the lateral feed requirements of the disclosed device, laparoscopic use of the preferred embodiment of the sprayer assembly device shown in FIGS. 1–9 is not possible. In fact, FIG. 10 teaches an alternate embodiment, showing the invention in conjunction with, for example, a catheter for possible laparoscopic procedures. In the alternate embodiment the spray assembly using the MBU is replaced with an intermediate plate 94 having multiple fluid paths (96, 98, 100, and 102) and a sprayer plate 104 with exit ports 106 and 108. The exit ports 106 and 108 are disclosed as analogous to the ports 72 and 74 of the MBU sprayer assembly (FIG. 9). However, the disclosed laparoscopic embodiment lacks the spin chamber, sloped walls, and other dimensional requirements provided by the present invention to achieve the proper circumjacent spray pattern of the two fluids, thereby substantially eliminating the occurrence of unreacted fibrinogen.

Likewise, the '596 patent relates to a dual fluid applicator assembly. While the invention disclosed is directed to proper mixing of a fibrinogen solution with a thrombin solution on a surface, it attempts to achieve this goal using a sterile gas. The '596 patent does not achieve a circumjacent spray of the two solutions, and does not make use of the unique properties provided by the MBU structure of the present invention.

Finally, a device sold by Johnson & Johnson provides for the application of a bovine thrombin and calcium chloride solution to a wound. In addition to possible issues raised by the use of bovine proteins, this procedure does not provide a satisfactory hemostasis function in high blood flow situations. The thrombin is believed to be washed from the wound site by the flow of blood.

The present invention, as set forth in the appended claims, overcomes these and other problems in prior art devices.

DISCLOSURE OF INVENTION

The present invention provides a medical device for delivering volumetric quantities of a first and a second biochemically reactive fluid. An embodiment or device comprises a first container having an opening and adapted to contain the first biochemically reactive fluid. A second container of this embodiment has a second fluid opening adjacent the first fluid opening and is adapted to contain the second biochemically reactive fluid. A spray unit is preferably in fluid communication with the first container and the second container, the spray unit being capable of separately atomizing the first and second biochemically reactive fluids into an aerosol with at least one energy source of either a liquid energy, a mechanical energy, a vibration energy, or an electric energy. A fluid pressurizer is preferably associated with the first and second containers for pressurizing the first and the second containers for delivery of the biochemically reactive fluids under pressure through the spray unit onto a surface. Wherein the first and second biochemically reactive fluids initially mix outside the delivery device (both in the air and on the surface).

The invention of the present application may be used to deliver biologicals such as collagen, photoactivable collagen, thrombin, photoactivable thrombin, tPA, photoactivable tPA, plasmin, photoactivable plasmin, urokinase, photoactivable urokinase, Factors VII, IX, X and XI, photoactivable Factors VII, IX, X and XI, albumin, photoactivable albumin, growing factors, cells, and fibrin. The following discusses the invention solely in terms of fibrin delivery, but those skilled in the art would understand its broader applications using other biologicals as well.

The present invention also provides a method for delivering fibrin to a surface. One embodiment method comprises the steps of: providing a liquid solution of fibrinogen, a liquid solution of thrombin, and a spray unit in fluid communication with the fibrinogen and thrombin solutions. The method further comprises spraying the fibrinogen solution and the thrombin solution separately onto the surface and mixing for the first time the fibrinogen with the thrombin on the surface to make fibrin.

This invention also provides a method for delivering fibrin to a surface within a cavity of a body of an animal to prevent the formation of adhesions. One embodiment of the method comprises a liquid solution of fibrinogen, a liquid solution of thrombin, and a spray unit in fluid communication with the fibrinogen and thrombin solutions. This method further comprises spraying the fibrinogen solution and the thrombin solution separately onto the surface with the spray unit, mixing for the first time the fibrinogen with the thrombin on the surface to make a fibrin film capable of preventing the formation of adhesions.

Preferably the medical devices of this invention operate at pressures that are generated by a hand-held device. This allows the present device to provide a cost effective and less complicated alternative to those medical devices that rely on pressurized gasses as a means for atomizing fluids and conveying them to a surface to be treated.

It is contemplated that versions of the medical device may be used in open-type surgeries such as laparotomic surgeries, topically and in minimally invasive surgeries such as laparoscopic surgeries. In open-type surgeries and minimally invasive surgeries, the present device may be used to achieve hemostasis, promote wound healing and for anti-adhesion purposes. In topical applications, the device may be used for treating burn patients during skin grafting procedures by delivering fibrin glue acting as a drug delivery vehicle for antimicrobial agent.

Specifically, with respect to laparoscopic surgeries, the present invention provides an embodiment of the delivery device using a spray assembly capable of delivering two reactive fluids through, for example, a catheter to be properly applied within the body cavity without the remnant of unreacted fluids. The delivery of one reactive fluid in a circumjacent cone with the other reactive fluid effects the desired mixing.

The disclosed medical devices are capable of simultaneously or sequentially delivering biochemically reactive fluids to a surface where they mix for the first time. In the sequential application, it is possible to repeat the procedure to incrementally form a fibrin film.

BRIEF DESCRIPTION OF DRAWINGS

FIG. 1 is a schematic view of the device of this invention;

FIG. 2 is another embodiment of the device of this invention;

FIG. 3 is an assembly view in perspective of a spray unit;

BEST MODE FOR CARRYING OUT THE INVENTION

While the invention is susceptible of embodiment in many different forms, there is shown in the drawings and will herein be described in detail, preferred embodiments of the invention with the understanding that the present disclosure is to be considered as an exemplification of the principles of the invention and is not intended to limit the broad aspect of the invention to the embodiments illustrated.

This invention provides a method and apparatus for delivering two biochemically reactive liquids, preferably fibrinogen and thrombin, to form fibrin. These biochemically reactive fluids may be delivered topically, in open-type surgeries, such as laparotomic surgeries and in minimally invasive surgical techniques such as, for example, laparoscopically. While it is well known to use fibrin for hemostasis purposes, it has been found that fibrin can be used to prevent the formation of adhesions in cavities of the human body. It is possible to manipulate the concentrations of both fibrinogen and thrombin, especially thrombin, to effect a change in the characteristics of the resultant fibrin film. One such characteristic is the pore size of the film. By manipulating the concentrations of these fluids one can tailor the fibrin film that is best suited for its intended end use.

Many details including specific examples and test results of such manipulations of concentrations and the like are discussed in U.S. Pat. No. 5,989,215, issued Nov. 23, 1999 to the Assignee of the present invention. The entire disclosure of the '215 patent is hereby incorporated by reference.

Delivery Device—Generally

Figure 1:
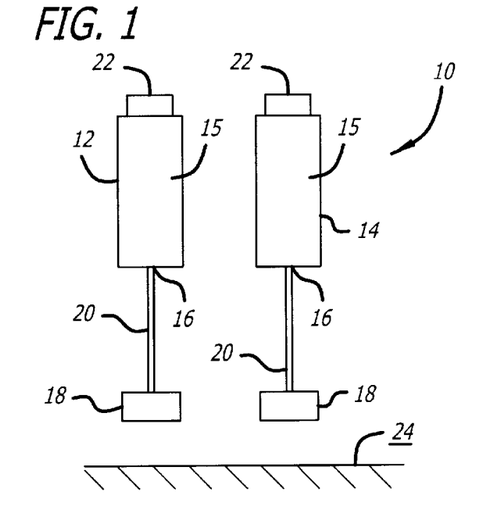

FIG. 1 shows a schematic representation of a device 10 having a first container 12 and a second container 14. Each of the containers have a fluid channel 15 and a fluid opening 16. The opening 16 of each of the first and second containers 12 and 14 is associated with a spray unit 18. The spray unit 18 may be directly attached to the first and second containers 12 and 14 or may be connected by other means such as a flexible medical tubing 20. A pressurizer 22 is associated with each of the first and second containers 12 and 14 for pressurizing fluids contained therein for delivery to a surface 24. It is possible to have a single pressurizer for both containers.

Figure 2:
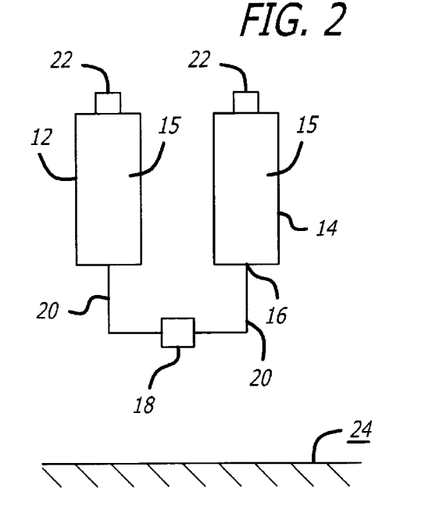
Figure 3:
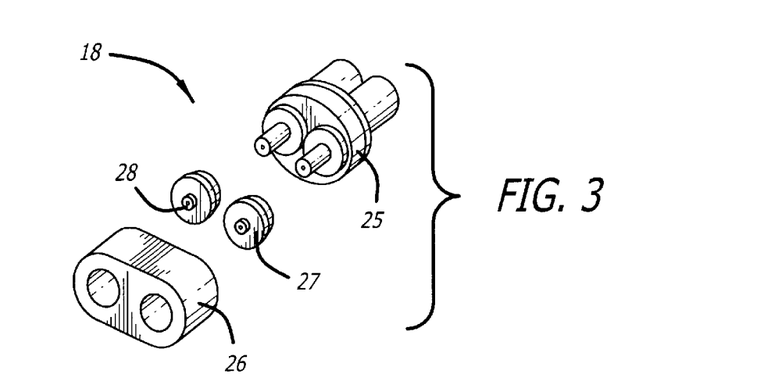
Figure 4:
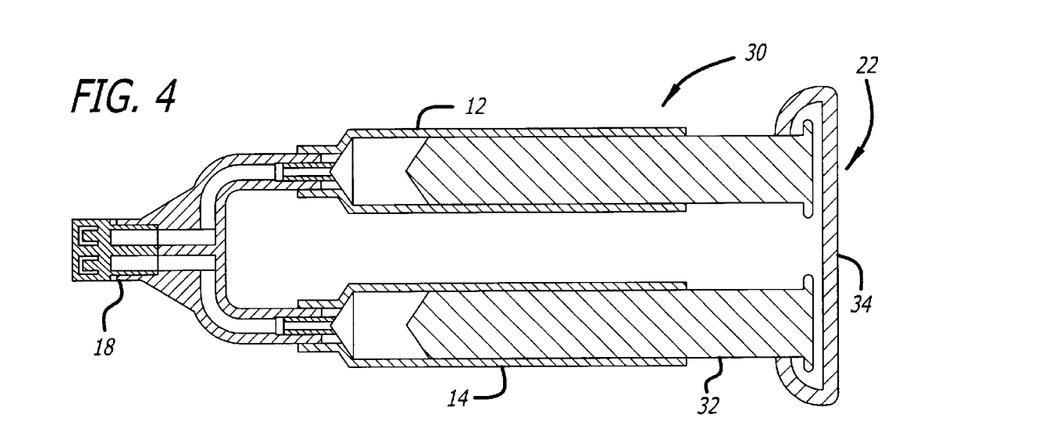
FIG. 4 is a perspective view of the device of this invention for open-type surgeries such as laparotomic uses.

FIG. 2 shows a delivery device having a single spray unit 18. FIG. 3 shows that the spray unit 18 is an assembly of several parts typically having an input piece 25, and an output piece 26 together encompassing two mechanical break-up units (MBU) 27. Preferably the pieces 25 and 26 snap fit together for ease of assembly.

The MBU 27 are known in the art as pressure swirl atomizers. Generally speaking, each MBU has an inner surface having three converging tangential channels that define a fluid path that rotates in a counter-clockwise direction as viewed from an inside surface of the MBU outward. The channels direct the incoming fluid to a spin chamber to generate angular momentum in the fluid. The spinning fluid exits the MBU through a port 28 to form an aerosol.

It may be desirable to have one MBU 27 having channels that follow a clockwise path and another adjacent MBU 27 that has channels that travel counterclockwise. It is also possible that the MBU 27 have from 2–4 channels or more per spray unit 18.

Several presently preferred MBU are available from Seaquist Dispensing of Cary, Ill. under the product designations CS-5512, CS-5501, and CS-5503.

The device shown in FIG. 1 has a single MBU 27 per spray unit 18. The device shown in FIG. 2 has two MBU 27 per spray unit 18. Of course it is possible to incorporate more than two MBU per spray unit 18.

Generally, it is possible to use several different energy types to form an aerosol from the biochemically reactive fluids. The preferred energy types are those selected from the group consisting of liquid kinematic energy, mechanical energy, vibration energy, and electric energy. This group excludes gas energy which is employed in U.S. Pat. No. 4,631,055 because (1) the mechanisms necessary to generate the gas energy may be expensive; and (2) because the momentum of the gas energy stream that atomizes the fluids may be incompatible with and cause damage to certain delicate human tissues. Mechanisms capable of generating these energies and separately atomizing fluids may be referred to in the claims as a means for separately atomizing first and second fluid streams or the like.

Atomizers that use liquid kinematic energy are the preferred devices for generating an aerosol spray and include swirl atomizers and most preferably pressure-swirl atomizers such as the MBU 27 described above. An example of an atomizer employing mechanical energy includes rotary atomizers such as impellers or pumps. An example of devices employing vibration energy include acoustic and ultrasonic devices. An example of devices employing electric energy to create an aerosol spray include electrostatic devices. These are all well recognized energy sources for atomizing liquids as set forth in *Liquid Atomization*, pg. 2, by L. Bayvel and Z. Orzechowski.

These atomizing devices could also include a piezoelectric crystal that meters out small droplets of fluid based upon a cycle time of the piezoelectric crystal.

Preferably, the spray unit 18 has a diameter of 10 mm or less so that it may be passed through standard trocar devices which typically have diameters of from about 10 mm–12 mm. Trocars are used to access internal cavities of an animal body during minimally invasive surgeries. The input device 25 shown in FIG. 3 has an external diameter of less than about 10 mm–12 mm.

It important that there be proper spacing between the two MBU 27 to achieve mixing of the two biochemically reactive fluids on the surface 24. However, also important is that the spacing be sufficient to prevent mixing at the discharge port 28 of each MBU 27. Such mixing would cause 110 fibrin to form at the exit port 28 thereby clogging the device 10. This invention further contemplates the possibility of a barrier wall (not shown) separating each MBU to prevent such mixing.

As shown in FIG. 4, the containers 12 and 14 are preferably syringes attached together or integral with one another to define a single unit 30. The syringes are preferably of a size commonly available and of volumes from about 1–20 cc, most preferably about 110 cc. It is also preferable that the containers 12 and 14 have equal volumes.

The pressurizer 22 in this embodiment is a dual plunger having two horizontally spaced plungers 32 mechanically coupled at one end by a crossbar 34. The embodiment of FIG. 4 may be modified such that distal ends of the containers 12 and 14 are dimensioned to fit directly into rear inlet ports 35 on the input device 25 (FIG. 3).

It should be understood that in place of the syringes, this invention contemplates using pipettes or other devices that are capable of dispensing accurate and determined volumes of liquid. One presently preferred pipette is a repeatable pipette sold by Eppendorf. The pressurizer could also be other devices capable of generating fluid pressure within a container such as a pump. The invention also contemplates using more than two containers to deliver additional fluids to the surface 24.

Delivery Device–Minimally Invasive Surgery

FIG. 5 shows the medical device 10 adapted for use in minimally invasive surgical applications. Device 10 has medical tubing 20 which extend from the first and second containers 12 and 14 through a sleeve 72. The sleeve 72 extends through a trocar 70 which is inserted into a surgical opening of an animal body to provide access to a cavity of the animal. In this fashion the spray unit 18 may be directed into the animal cavity to treat a wound therein.

This invention contemplates providing an articulatable joint (not shown) at a distal end of the device 10 which may be controlled by medical personnel outside the animal cavity to position the spray unit 18 to face a wound or surface to be treated with the device 10.

A preferred embodiment of the device of the present invention utilizes an MBU unit which can be used preferably with a 5 mm trocar. Dual MBU in a side-by-side configuration were believed to effect proper delivery of the reactive fluids. It was, therefore, necessary to overcome the dimensional limitations presented by a 5 mm envelope. Further, the MBU used needed to be consistent with the following parameters: fluid density (1/cc), viscosity (1 and 8 cp), pressure (58 psi/400 kPa), flowrate (0.4 cc/s), and spray cone angle (60°).

Referring to FIGS. 9 through 12, a preferred embodiment includes a fluid delivery device comprising MBU 230, two feed conduits 210, and two feed ports 220. The feed conduits 210 deliver fluid to the feed ports 220 of the MBU, which then direct the fluid to a spin chamber 240. The spin chamber 240 has a first funneling portion 250 having a sloped sidewall 260 for directing fluid from the first spin chamber 240 into a first exit port 270. Due to the space limitations of the present spray tip invention, the feed conduits 210 are positioned adjacent the spin chamber 240 and are generally parallel to the exit port 270.

The fluid delivery device of the present embodiment preferably includes two such units and may include additional paths for additional features, such as optical fibers 280 (FIG. 11) or other fluid application assisting devices. The use of optical fiber 280 would allow a light source to focus on the wound location for improved viewing, enzyme activation, or both. The device is preferably dimensioned in such a manner that it produces spray from both of the exit ports 270 when fluids of different viscosities are fed into each mechanical breakup unit 230 and a force of a single magnitude is used to force fluid through the device. For example, fibrinogen and thrombin require different pressures to achieve the same exit velocity, and thus require differing dimensions of the two paths in order to achieve a desired flow rate for a given force applied to the device.

For laparoscopic purposes, a flow rate of approximately 0.4 to 0.5 cc/second is desirable. The fluids exit the exit ports 270 as spray cones, as shown in FIG. 9. It is desirable to achieve a spray cone of thrombin which is circumjacent the fibrinogen spray cone so that no unreacted fibrinogen is applied to the surface. Thus, at a distance approximately 1 inch from the exit port 270, it is preferable to achieve a spray cone of thrombin which covers the entire cone of fibrinogen.

In order to achieve this coverage, it may be preferable to orient the feed ports 220 in opposite rotational directions between two MBU. The feed ports 220 may have any number of shapes, for example they may be spiral shaped or polygonal.

Referring to FIGS. 9 and 10, the device comprises several variable parameters. Table 1A below sets forth exemplary measurements for three embodiments of the present invention. The variable "D" represents the diameter of the spin chamber 240, while "t" is the depth, and "A" is the included angle of the funneling portion 250. Further, the variable "d" indicates the diameter of the exit port 270 while "L" indicates the length. Finally, "W" is the width of the feed port 220 and "h" is the height.

Various preferred devices are designated in Table 1A as: (a) flat feeder; (b) nominal; and (c) reduced spin chamber. The nominal device entry illustrates standard device dimensions. The flat feeder is so designated because of the shorter height of feed port 220, relative to that of the nominal design. Finally, the reduced spin chamber device has a reduced diameter of spin chamber 240 relative to the nominal device.

TABLE 1A

Dimensions of Three Designated MBU in inches (mm)

| Designation | D | t | A | d | L | W | h |
|---|---|---|---|---|---|---|---|
| a) Flat Feeder | 0.0430 (1.09) | 0.0165 (0.421) | 120° | 0.0078 (0.198) | 0.010 (0.25) | 0.0122 (0.31) | 0.0094 (0.24) |
| b) Nominal | 0.0430 (1.09) | 0.0165 (0.420) | 120° | 0.0078 (0.198) | 0.010 (0.25) | 0.0108 (0.31) | 0.0108 (0.27) |
| c) Reduced Spin Chamber | 0.0380 (0.970) | 0.0165 (0.420) | 120° | 0.0078 (0.198) | 0.010 (0.25) | 0.0122 (0.31) | 0.0094 (0.24) |

For testing purposes, prototype dual MBU (DMBU) or spray tips were created. The dimensional parameters of these test units are set forth in TABLE 1B below.

TABLE 1B

Dimensions of Test DMBU in inches (mm)

| Designation | D | t | A | d | L | W | h |
|---|---|---|---|---|---|---|---|
| DMBU 0a | 0.039 (0.99) | 0.016 (0.41) | 115° | 0.0067 (0.170) | 0.032 (0.81) | 0.014 (0.36) | 0.010 (0.25) |
| DMBU 0b | 0.0390 (0.99) | 0.016 (0.41) | 115° | 0.0072 (0.183) | 0.038 (0.97) | 0.015 (0.38) | 0.012 (0.30) |
| DMBU Ia | 0.045 (1.14) | 0.016 (0.41) | 113° | 0.009 (0.23) | 0.028 (0.71) | 0.017 (0.43) | 0.004 (0.10) |
| DMBU Ib | 0.043 (1.09) | 0.018 (0.46) | 113° | 0.010 (0.25) | 0.025 (0.64) | 0.017 (0.43) | 0.008 (0.20) |
| DMBU IIa | 0.045 (1.14) | 0.020 (0.51) | 119° | 0.010 (0.25) | 0.015 (0.38) | 0.013 (0.33) | 0.0086 (0.22) |
| DMBU IIb | 0.044 (1.12) | 0.020 (0.51) | 110° | 0.010 (0.25) | 0.013 (0.33) | 0.013 (0.33) | 0.0096 (0.24) |

Figure 13:
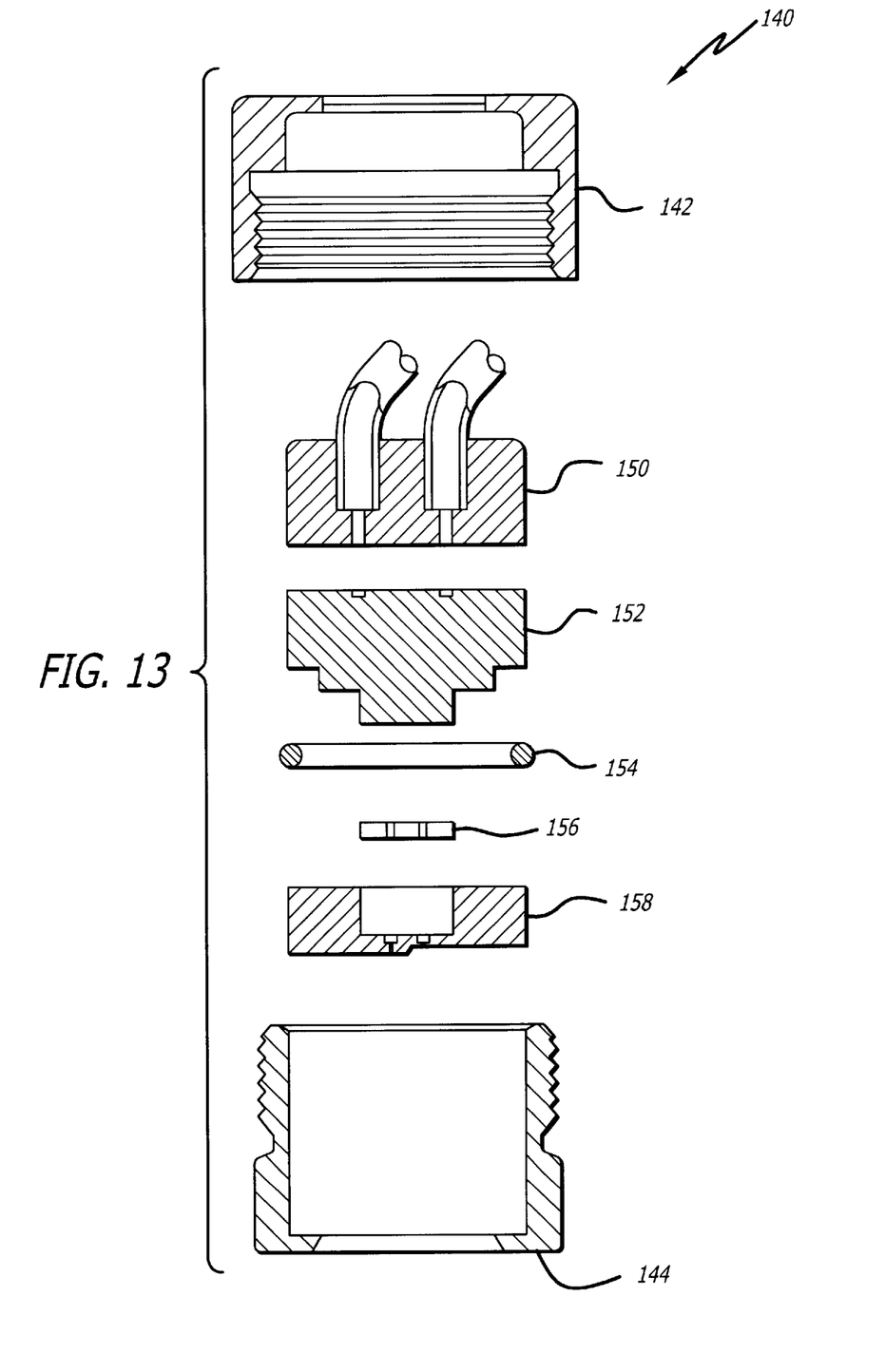
FIG. 13 is an exploded cross-sectional view showing the various components of the fixture used to test the spray tips of the present invention.
Figure 14:
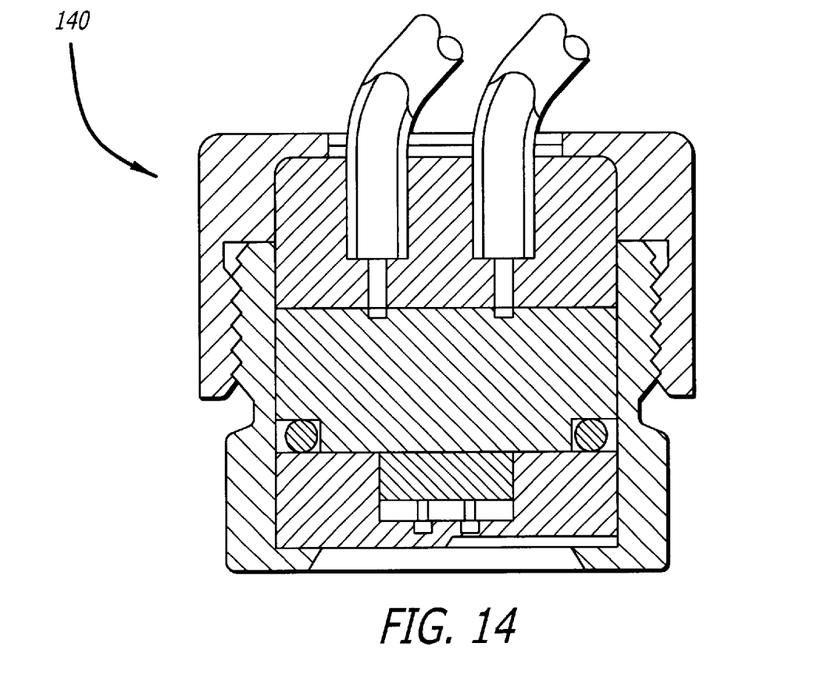
FIG. 14 is a side cross-section of the assembled test fixture.

A test fixture 140 was designed which permitted complete flexibility in the choice of spray-generating geometry. Except for the functional geometry of the DMBU, the test fixture 140 did not embody any size, fabrication, or assembly features of the anticipated delivery device. FIG. 13 illustrates an exploded view of the components used for the fixture to test the DMBU devices. The test fixture 140 includes a two-piece threaded housing cap 142 and housing base 144—measuring about one-inch (25 mm) tall by 1⅛ inch (29 mm) in diameter when assembled with a 12 inch (13 mm) circular cut-out in the top of the housing cap 142 and the bottom of the housing base 144—fluid source interface 150, a flow divider 152, an O-ring 154, a gasket 156, and an dual MBU 5 mm envelope 158. FIG. 14 shows the assembled test fixture 140.

Three variations of inserts were made for the fixture 140. The first configuration allowed the use of a single MBU. The second accommodated the dual MBU design, but fed both MBU with the same fluid simultaneously. The third insert provided means for feeding each MBU in the dual MBU geometry separately. FIG. 14 illustrates the last configuration.

Figure 15:
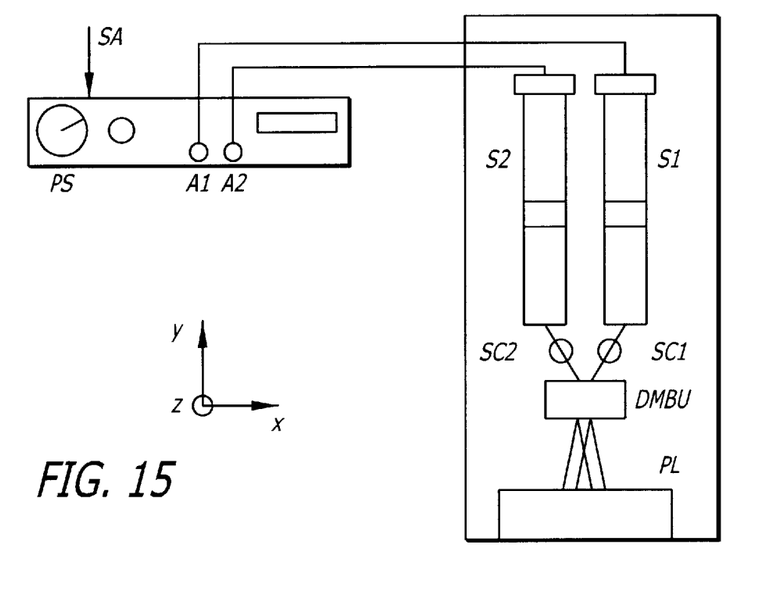
FIG. 15 is a schematic showing the spray generation components of the experimental set-up for testing the DMBU spray tips of the present invention.
Figure 16:
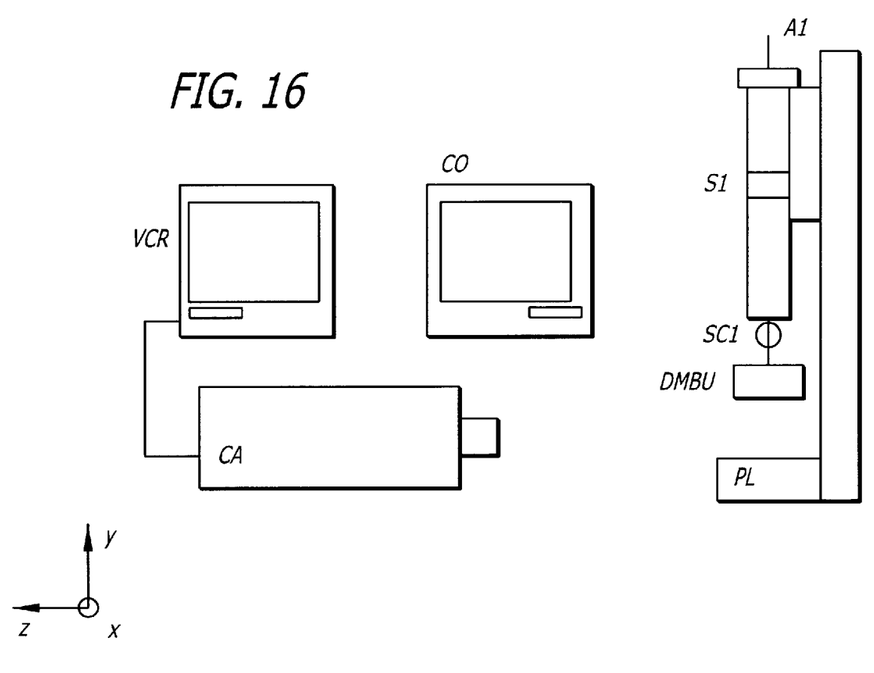
FIG. 16 is a schematic showing the recording components of the experimental set-up for testing the DMBU spray tips.
Figure 17:
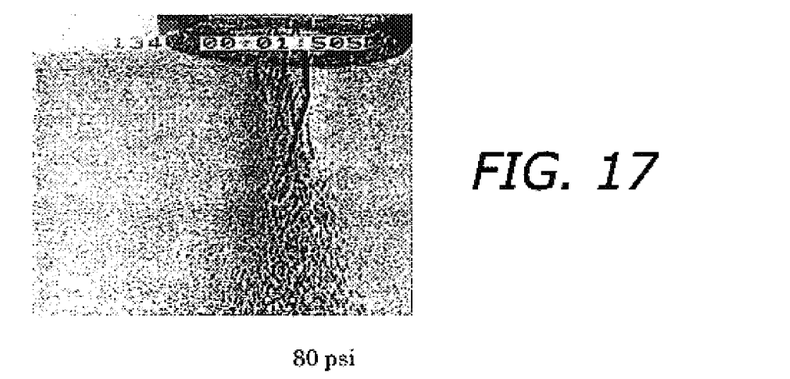
FIG. 17 is a macrograph of the spray from the DMBU II at 80 psi.
Figure 18:
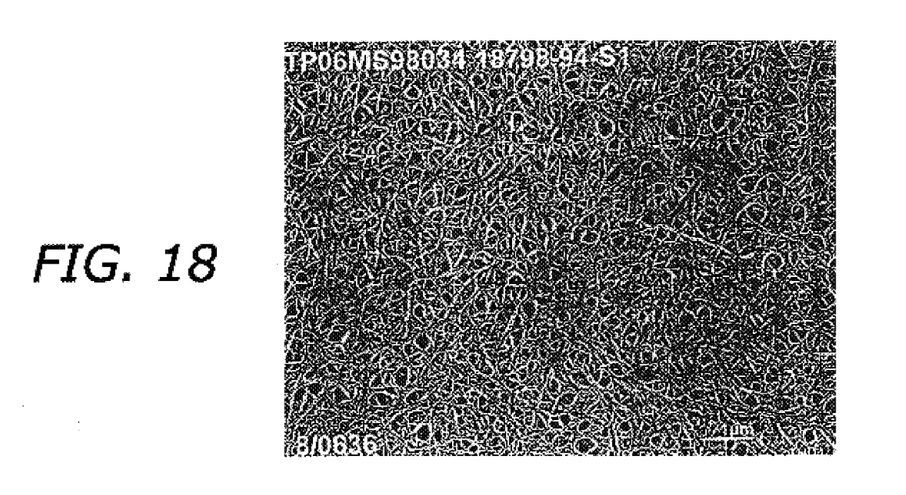
FIG. 18 is an SEM observation of the resulting fibrin micro-structure generated by DMBU II at 80 psi.

Referring to FIGS. 15 and 16, a front view and a side view of the layout of the test set-up apparatus are illustrated. Air pressure driven dispensing syringes, S1 and S2, are employed to generate separate liquid sprays through prototyped double mechanical break-up units (DMBU). The pressure is provided through an adjustable pressure source (PS) that is able to provide air pressures in the 0 to 100 psi range. The duration of pressure application could be adjusted automatically through an embedded electronic timer, or manually with a foot pedal. The minimum time interval is 0.1 seconds. The pressure source (PS) provided two separate air streams, A1 and A2, at identical pressures.

The air lines connected to corresponding syringes, S1 and S2, containing low and high viscosity liquids, respectively. Dispensing equipment (syringes, air and liquid lines, stopcocks (SC1 and SC2) and DMBU) were mounted on a vertical backplate (PL) during spray experiments. The spray field was recorded with a high speed video camera (CA) and recorded onto VHS video tapes (VCR), at a rate of about 200 frames per second. Recorded images were digitized using video/card and frame grabbing software on a computer (CO).

Figure 5:
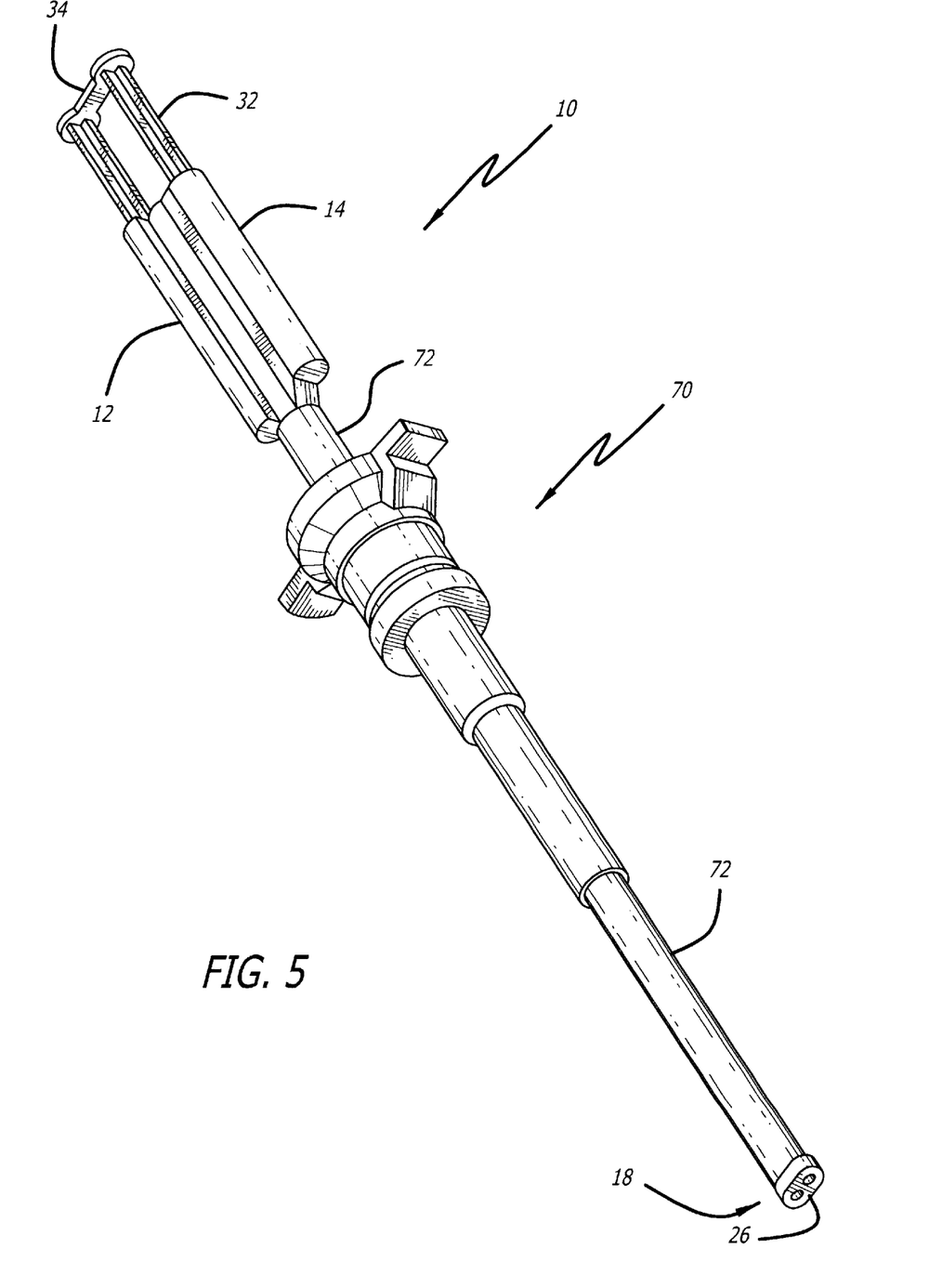
FIG. 5 is a perspective view of the device of the present invention for use in minimally invasive surgical techniques.
Figure 6A:
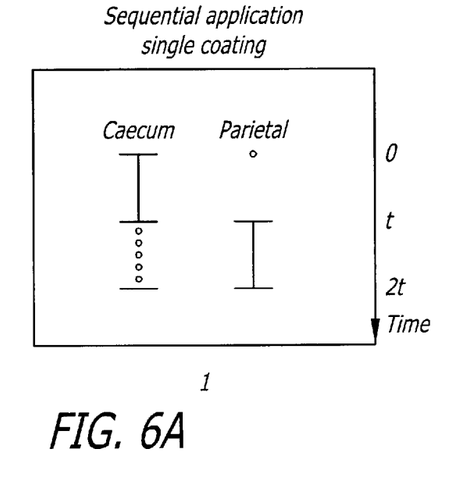
FIGS. 6A–6D are schemes showing the different types and modes of application using fibrin glues.
Figure 6B:
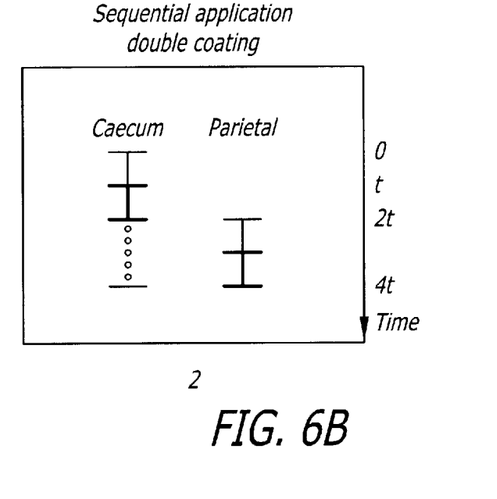
Figure 6C:
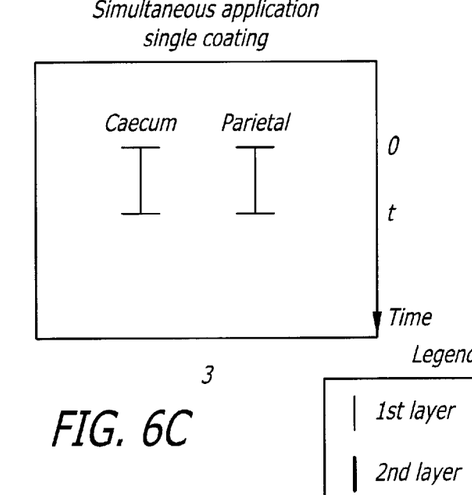
Figure 6D:
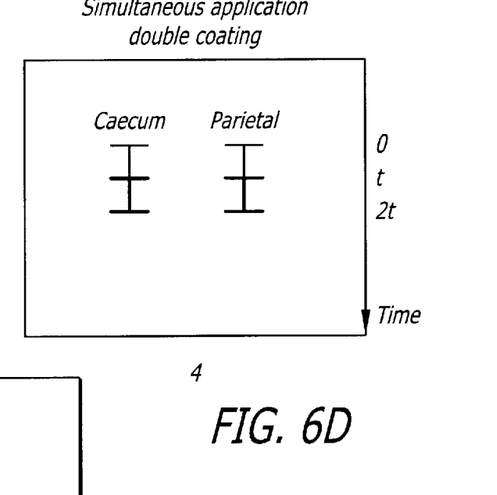
Figure 7:
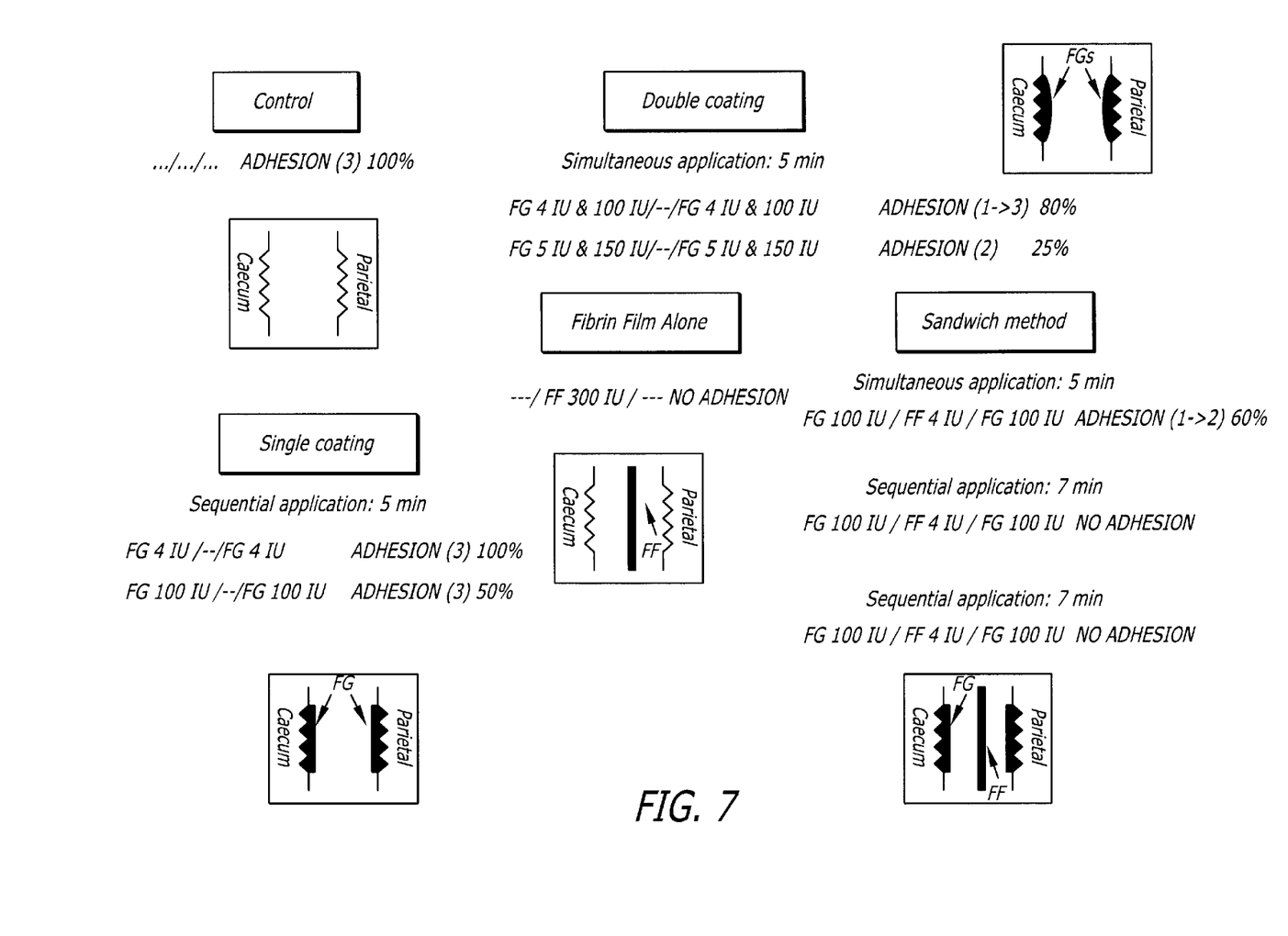
FIG. 7 is a scheme summarizing the different embodiments of the invention according to the different experimental approaches.
Figures 8A, 8B:
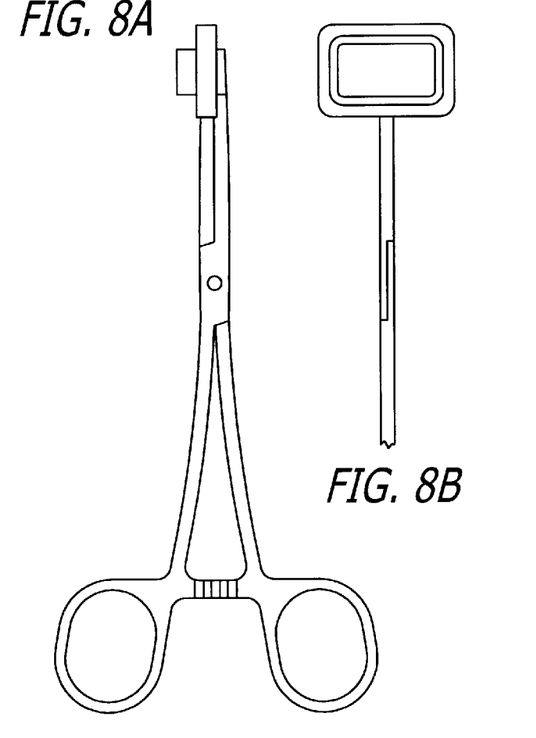
FIGS. 8A–8E are technical drawings showing different views of the clamp having been used in the course of the animal model.
Figure 8C:
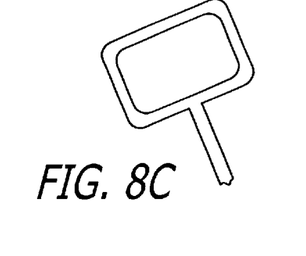
Figure 8D:
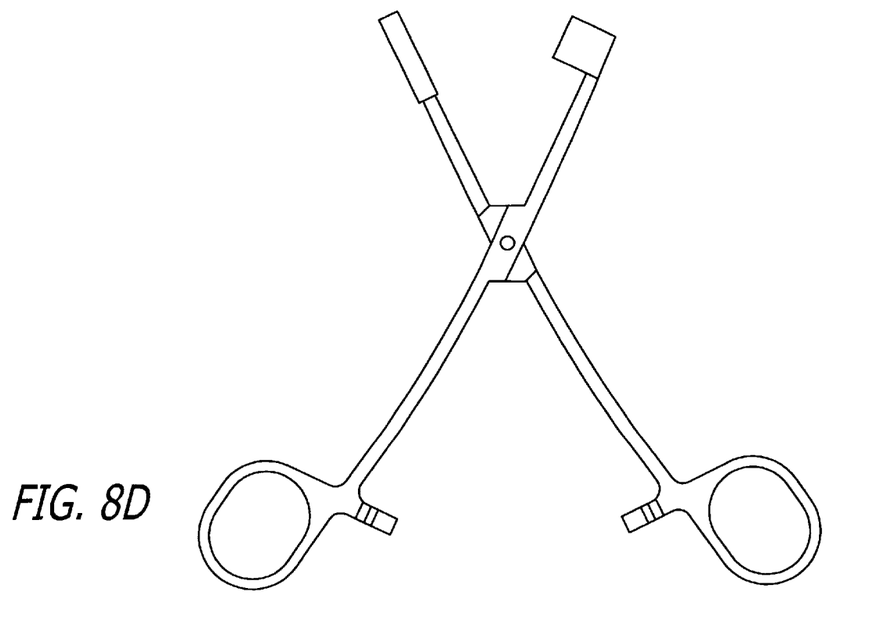
Figure 8E:
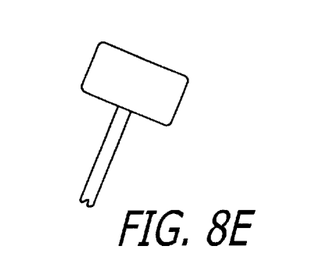
Figure 9:
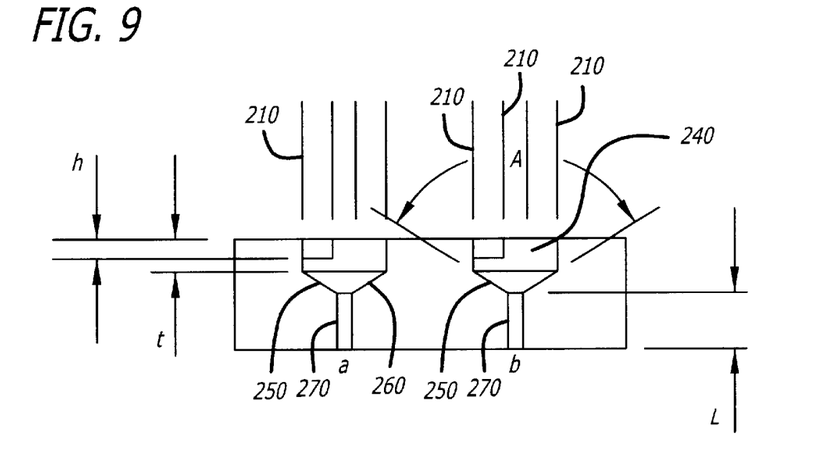
FIG. 9 is a cross-sectional side view taken through line A—A of FIG. 10 showing one embodiment of the assembly of the present invention.
Figure 10A:
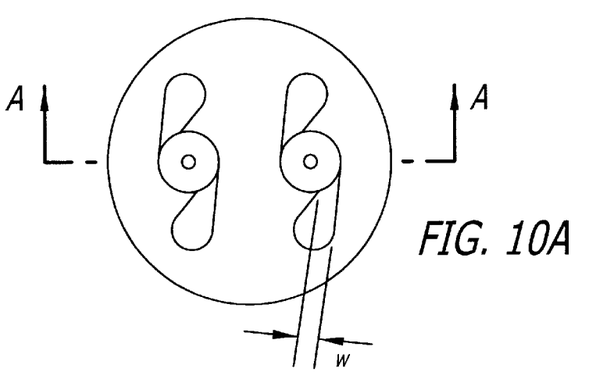
FIG. 10A is a plan view of one embodiment of an assembly of the present invention.
Figure 10B:
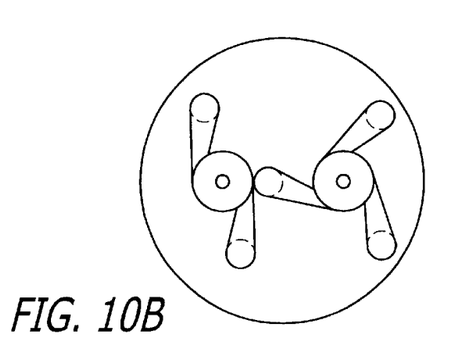
FIG. 10B is a plan view of another embodiment of an assembly of the present invention.
Figure 11:
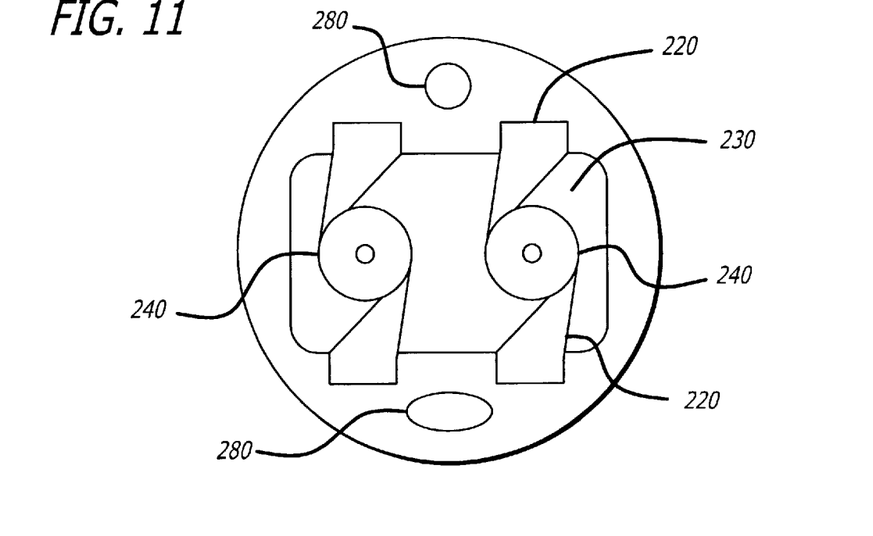
FIG. 11 is an internal view of one embodiment of the assembly illustrating the use of additional lumens for the incorporation of, for example, fluid or optical fibers.
Figure 12:
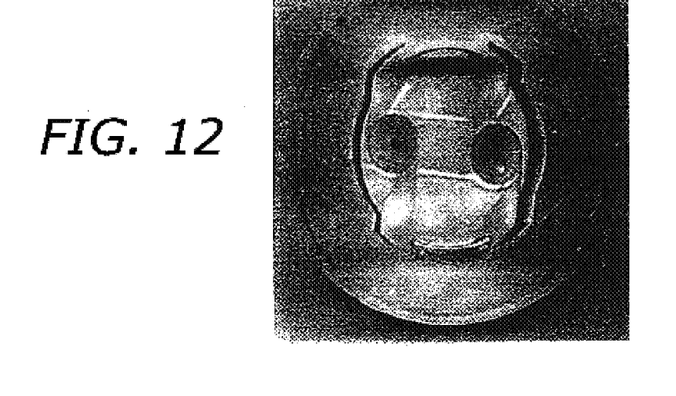
FIG. 12 is an internal view of one embodiment of the delivery device of the present invention.

For the test procedure, results from each of the DMBU were obtained using simulated liquids. Sterile water (1 cp) was used for thrombin, and a water/glycerol solution (8 cp) was used for fibrinogen. Each unit was tested at a driving pressure of 40, 60, and 80 psi. Based on a study of the recorded spray characteristics exhibited by each unit at the three pressures, DMBU II produced acceptable sprays at 60 psi and above. Hence, the feasibility of spraying two liquids with different viscosities from the present invention was demonstrated.

Further testing of the DMBU II using biologicals was performed. The solutions included a dilution of fibrinogen 1:2 with saline and thrombin with calcium chloride (170 IU/mL). FIG. 17 is a macrograph showing the resultant spray from DMBU II at 80 psi. FIG. 18 shows an SEM analysis of the resulting fibrin micro-structure generated by the DMBU II at 80 psi. The SEM shows an homogeneous and tight structure similar to fibrin barrier material produced with other non-laparoscopic devices.

While the MBU dimensions may vary from those listed in TABLE 1B, it is certain dimensional ratios which affect the preferred results of the present invention. In preparing an effective DMBU, the following dimensional ratios are of interest: W:h, D:d, D:t, L:d, t:L, and $V_{sc}$:$V_{ep}$, where $V_{sc}$ is the volume of the spin chamber (using the formula $\pi r^2 l$ for the volume of a cylinder) and $V_{ep}$ is the volume of the exit port. The preferred range for each of these ratios is from about 0.9 to about 1.5 for W:h, from about 3 to about 6 for D:d, from about 2 to about 4 for D:t, and from about 0.25 to about 2.0 for L:d.

In minimally invasive surgical applications, the invention provides a method for delivering fibrin to a surface of an animal to be treated, or to isolate one surface from another, to prevent the formation of adhesions. The method comprises the steps of providing a liquid solution of fibrinogen, a liquid solution of thrombin having a concentration from 3–10,000 IU/ml, and more preferably from 200–500 IU/ml, in a spray unit. The spray unit should be capable of separately atomizing the fibrinogen and the thrombin into an aerosol with an energy selected from the group consisting of liquid kinematic energy, mechanical energy, vibration energy, and electric energy. Further, the method comprises spraying the fibrinogen solution and the thrombin solution separately onto the surface and mixing the two solutions on the surface to make a fibrin film, in situ. This film is capable of preventing the formation of adhesions. The trocar 70 and sheathe 72, described above and shown in FIG. 5, may be used to provide access to the animal cavity.

While specific embodiments have been illustrated and described, numerous modifications are possible without departing from the spirit of the invention, and the scope of protection is only limited by the scope of the accompanying claims.

We claim:

1. A fluid delivery device for use in minimally invasive surgical procedures comprising:
   A) a tubular component having a distal end for insertion into a body cavity;
   B) a spray tip assembly having a diameter of at most about 12 mm and attached to the distal end of the tubular component for discharging fluid into the body cavity, the spray tip assembly comprising:
      a first mechanical breakup unit having at least one feed port configured to direct a fluid into a first spin chamber and issue into a first exit port; and
      a second mechanical breakup unit positioned alongside the first mechanical breakup unit and having at least one feed port configured to direct a fluid into a second spin chamber and issue into a second exit port, wherein the first and second exit ports extend through an external surface of the spray tip; and
   C) a first fluid source in fluid communication via the tubular component with two first feed conduits for delivering fluid to the first mechanical breakup unit and a second fluid source in fluid communication via the tubular component with two second feed conduits for delivering fluid to the second mechanical breakup unit, wherein the first and second feed conduits deliver fluid to different mechanical breakup units.

2. A fluid delivery device for use in minimally invasive surgical procedures comprising:
   A) a tubular component having a distal end for insertion into a body cavity;
   B) a spray tip assembly having a diameter of at most about 12 mm and attached to the distal end of the tubular component for discharging fluid into the body cavity, the spray tip assembly comprising:
      a first mechanical breakup unit having at least one feed port configured to direct a fluid into a first spin chamber and issue into a first exit port; and
      a second mechanical breakup unit positioned alongside the first mechanical breakup unit and having at least one feed port configured to direct a fluid into a second spin chamber and issue into a second exit port, wherein the first and second exit ports extend through an external surface of the spray tip; and
   C) a first fluid source in fluid communication via the tubular component with two first feed conduits for delivering fluid to the first mechanical breakup unit and a second fluid source in fluid communication via the tubular component with two second feed conduits for delivering fluid to the second mechanical breakup unit, wherein the first and second feed conduits deliver fluid to different mechanical breakup units, and wherein the first and second feed conduits are adjacent the spin chambers and parallel to the first and second exit ports.

3. A fluid delivery device for use in minimally invasive surgical procedures comprising:
   A) a tubular component having a distal end for insertion into a body cavity;
   B) a spray tip assembly having a diameter of at most about 12 mm and attached to the distal end of the tubluar component for discharging fluid into the body cavity, the spray tip assembly comprising:
      a first mechanical breakup unit having at least one feed port configured to direct fluid into a first spin chamber and issue into a first exit port; and
      a second mechanical breakup unit positioned alongside the first mechanical breakup unit and having at least one feed port configured to direct a fluid into a second spin chamber and issue into a second exit port, wherein the first and second exit ports extend through an external surface of the spray tip;
   C) a first fluid source in fluid communication via the tubular component with two first feed conduits for delivering fluid to the first mechanical breakup unit and a second fluid source in fluid communication via the tubular component with two second feed conduits for delivering fluid to the second mechanical breakup unit, wherein the first and second feed conduits deliver fluid to different mechanical breakup units;
   wherein the feed ports direct fluid from the first and second feed conduits to the spin chamber of each mechanical breakup unit, and wherein the feed ports of each mechanical breakup unit are oriented such that the first fluid is caused to spin in a direction opposite the second fluid within the spin chambers.

* * * * *